United States Patent [19]
Faass

[11] Patent Number: 5,503,908
[45] Date of Patent: Apr. 2, 1996

[54] SELF-ADHESIVE NONWOVEN ELASTIC COMPRESSIBLE COMPOSITE MATERIAL

[75] Inventor: Judith K. Faass, Dahlonega, Ga.

[73] Assignee: Kimberly-Clark Corporation, Neenah, Wis.

[21] Appl. No.: 271,276

[22] Filed: Jul. 6, 1994

Related U.S. Application Data

[63] Continuation of Ser. No. 995,468, Dec. 22, 1992, abandoned.

[51] Int. Cl.$^6$ .................................................. C09J 7/02
[52] U.S. Cl. .................... 428/198; 128/882; 428/230; 428/231; 428/261; 428/290; 428/354; 602/58; 602/76; 602/77
[58] Field of Search .................... 428/261, 230, 428/231, 198, 354, 355, 288, 289, 290; 54/82, 80.1; 128/882, 898; 602/58, 76, 77

[56] References Cited

U.S. PATENT DOCUMENTS

| | | | |
|---|---|---|---|
| Re. 31,887 | 5/1985 | Hodgson | 428/343 X |
| 2,371,001 | 3/1945 | Stone | 117/161 |
| 3,039,893 | 6/1962 | Banigan Jr. et al. | 117/122 |
| 3,350,215 | 10/1967 | Jenard et al. | 117/37 |
| 3,575,782 | 4/1971 | Hansen | 161/141 |
| 3,649,436 | 3/1972 | Buese | 161/160 |
| 3,692,618 | 10/1972 | Dorschner et al. | 428/296 X |
| 3,697,315 | 10/1972 | Mine | 117/122 |
| 3,849,241 | 11/1974 | Butin et al. | 428/137 |
| 4,099,269 | 7/1978 | Porner | 54/82 X |
| 4,112,177 | 9/1978 | Salditt et al. | 428/304 |
| 4,207,885 | 6/1980 | Hampton et al. | 128/156 |
| 4,209,563 | 6/1980 | Sisson | 428/288 |
| 4,340,563 | 7/1982 | Appel et al. | 264/518 |
| 4,357,459 | 11/1982 | Runavot et al. | 428/261 X |
| 4,363,853 | 12/1982 | Imamura et al. | 428/480 |
| 4,414,970 | 11/1983 | Berry | 128/156 |
| 4,470,411 | 9/1984 | Hoyt, Jr. | 54/82 X |
| 4,484,574 | 11/1984 | DeRusha et al. | 128/156 |
| 4,552,802 | 11/1985 | Mechin | 428/255 |
| 4,663,220 | 5/1987 | Wisneski et al. | 428/288 X |
| 4,699,133 | 10/1987 | Schafer et al. | 128/156 |
| 4,720,415 | 1/1988 | Vander Wielen et al. | 428/286 X |

(List continued on next page.)

FOREIGN PATENT DOCUMENTS

| | | | |
|---|---|---|---|
| 45592 | 2/1982 | European Pat. Off. | |
| 336857A | 10/1989 | European Pat. Off. | |
| 341875 | 11/1989 | European Pat. Off. | |
| 0341875 | 11/1989 | European Pat. Off. | D04H 1/56 |
| 548609 | 6/1993 | European Pat. Off. | |
| 0548609 | 6/1993 | European Pat. Off. | B32B 5/04 |
| 90/00884 | 10/1991 | South Africa. | |

OTHER PUBLICATIONS

"Making Strides in Support," *The Blood–Horse*, Apr. 8, 1989, pp. 1938–1940
"Meltblown–Nonwoven Support Bandage," *Nonwovens Report International*, Feb. 1992, p. 6.

*Primary Examiner*—Jenna L. Davis
*Attorney, Agent, or Firm*—Karl V. Sidor

[57] ABSTRACT

Disclosed is a self-adhesive nonwoven elastic composite material composed of at least one elastic composite material; and a coating of a self-adhesive material on at least a portion of at least one exterior surface of the elastic composite material so that the material is capable of being compressed in the Z-direction at least about 45 percent at a pressure of about 3 psi to a thickness of not less than about 0.035 inch. The elastic composite material may contain an elastomeric nonwoven fibrous web joined to at least one relatively nonelastic gatherable material at spaced-apart locations so that the gatherable material is gathered between the spaced-apart locations. Such an elastic composite material can be coated with a self-adhesive material on at least a portion of at least one exterior surface of the elastic composite material so that the peel strength of the self-adhesive material is less than the peel strength of the layers of the elastic composite material. Also disclosed is a self-adhesive product in the form of a wrap or bandage for use in human or veterinary medicine.

16 Claims, 2 Drawing Sheets

U.S. PATENT DOCUMENTS

| | | | |
|---|---|---|---|
| 4,737,400 | 4/1988 | Edison et al. | 428/261 X |
| 4,741,949 | 5/1988 | Morman et al. | 428/288 X |
| 4,803,117 | 2/1989 | Daponte | 428/288 |
| 4,849,049 | 7/1989 | Colton | 156/291 |
| 4,863,779 | 9/1989 | Daponte | 428/152 |
| 4,879,169 | 11/1989 | Zafiroglu | 428/230 |
| 4,911,155 | 3/1990 | Delannoy | 128/155 |
| 4,926,848 | 5/1990 | Shimkus et al. | |
| 4,944,958 | 7/1990 | Langen et al. | |
| 4,949,668 | 8/1990 | Heindel et al. | 118/314 |
| 4,957,795 | 9/1990 | Riedel. | |
| 4,977,011 | 12/1990 | Smith. | |
| 4,984,584 | 1/1991 | Hansen et al. | 128/898 |
| 5,034,008 | 7/1991 | Breitkopf | 604/385,2 |
| 5,115,627 | 5/1992 | Scott | 54/82 |
| 5,116,662 | 5/1992 | Morman | 428/287 X |
| 5,156,589 | 10/1992 | Langen et al. | |
| 5,209,801 | 5/1993 | Smith. | |
| 5,230,701 | 7/1993 | Meyer et al. | |
| 5,266,394 | 11/1993 | Diehl et al. | 428/261 |

SELF-ADHESIVE NONWOVEN ELASTIC COMPRESSIBLE COMPOSITE MATERIAL

This application is a continuation application of application Ser. No. 07/995,468 filed on Dec. 22, 1992, abandoned.

FIELD OF THE INVENTION

The present invention relates to a self-adhesive fabric and a method of making the same.

BACKGROUND OF THE INVENTION

In the fields of human and veterinary medicine, wrappings or bandages have long been used to prevent injury, to protect against re-injury. For example, limbs are wrapped to prevent injury or re-injury to skin, tendons, muscles and/or ligaments as well as to provide support.

In the field of veterinary medicine, trainers have used bandages on horses' legs in order to protect against a condition called run-down. As a horse gallops or races, its tendons, ligaments, and bones can be temporarily subjected to loads exceeding 10,000 to 12,000 pounds. This load transfers over the horse's leg causing dorsiflexion of the fetlock (i.e., the lower portion of a horses leg called the fetlock flexes under the extreme load and drops or "runs down" touching the ground). If a horse runs down, it may abrade and tear open the back of its fetlock; a condition comparable to a severe friction burn on human skin. If a wounded fetlock becomes infected, a horse is likely to become lame, making training or racing impossible.

In the past, woven non-cohesive track wrapping bandages were used for protection both in the stable and on the racetrack. For example, a horse's fetlocks were wrapped to protect against run-down. Wrapping such bandages has been a major concern for the veterinarians and trainers. If the material folded or creased while being applied, the bandage might provide uneven support or have high tension areas. This ultimately could cause circulation problems in the horse's leg.

Wrapping products are typically employed so they apply a pressure of less than about 3 pounds per square inch to the area wrapped. Lower pressures such as, for example, about 1 psi are desirable. Wraps which exert substantial pressure can cause circulation problems. In some situations, wraps which are made of materials which are elastic and/or compressible may be useful to control the amount of pressure applied.

Self-adhesive nonwoven elastic wrapping products for horses such as Vetrap® and Equisport™ wraps, both available from the Minnesota Mining and Manufacturing Company generally offer improvements over woven, non-cohesive wraps such as better energy absorption and adherence to a limb due to the retractile force of the elastic material. These nonwoven elastic materials are generally less expensive than woven materials. However, strong self-adhesive properties in combination with elastic properties of certain nonwoven materials can make it difficult for a person, trainer or otherwise, to apply the bandage to an equine limb safely and correctly.

Some nonwoven wrapping products are latex saturated to provide elasticity and self-adhesive properties. However, latex saturation produces a rubbery feel and inconsistent bandage performance in adverse weather conditions (e.g., high heat and/or high humidity). Also, the latex saturation diminishes permeability to air and water vapor.

Other nonwoven wrapping products contain a series of parallel rows of elastic filaments running the full length of the product. In some situations, individual elastic filaments could create pressure points or areas of high tension which can be uncomfortable.

Self-adhesive products may be used alone or in combination with cushioning bandages. Such cushioning bandages are compressible and provide softness and comfort to a limb wrapped by an self-adhesive product. However, available self-adhesive products have failed to address the need for a material which is both self-adhesive and compressible enough to provide softness and comfort.

Self-adhesive wrapping bandages also have many applications outside veterinary medicine. For example, elastic wraps are used in human medicine. For example, in sports medicine, it is desirable prevent injury or re-injury to skin, tendons, muscles and/or ligaments as well as to provide support using materials that are inexpensive.

Thus, a need exists for an inexpensive material which is self-adhesive, elastic and compressible. There is also a need for a material having those properties which is relatively tough, durable, lightweight and relatively permeable to air and water vapor. For example, a need exists for a self-adhesive wrap or bandage composed substantially or entirely of materials such that bandage is elastic, compressible, relatively permeable to air and/or water vapor and so inexpensive as to be considered disposable.

DEFINITIONS

The term "elastic" is used herein to mean any material which, upon application of a biasing force, is stretchable, that is, elongatable at least about 60 percent (i.e., to a stretched, biased length which is at least about 160 percent of its relaxed unbiased length), and which, will recover at least 55 percent of its elongation upon release of the stretching, elongating force. A hypothetical example would be a one (1) inch sample of a material which is elongatable to at least 1.60 inches and which, upon being elongated to 1.60 inches and released, will recover to a length of not more than 1.27 inches. Many elastic materials may be elongated by much more than 60 percent (i.e., much more than 160 percent of their relaxed length), for example, elongated 100 percent or more, and many of these will recover to substantially their initial relaxed length, for example, to within 105 percent of their original relaxed length, upon release of the stretching force.

The term "nonelastic" as used herein refers to any material which does not fall within the definition of "elastic," above. The term "machine direction" as used herein refers to the planar dimension of a nonwoven fibrous web which is in the direction of travel of the forming surface onto which fibers are deposited during formation of the web.

The term "cross-machine direction" as used herein refers to the planar dimension of a nonwoven fibrous web which is in the direction that is perpendicular to the machine direction defined above.

The term "Z-direction" as used herein refers to the thickness direction of a sheet of material, that is, the direction perpendicular to the plane of the length and width dimensions.

As used herein, the term "disposable" is not limited to single use articles but also refers to articles that can be discarded if they become soiled or otherwise unusable after only a few uses.

The term "composite elastic material" as used herein refers to an elastic material which may be a multi-component material or a multilayer material. For example, a multilayer material may have at least one elastic layer joined to at least one gatherable layer at least at two locations so that the gatherable layer is gathered between the locations where it is joined to the elastic layer. Such a multilayer composite elastic material may be stretched to the extent that the nonelastic material gathered between the bond locations allows the elastic material to elongate. This type of multilayer composite elastic material is disclosed, for example, by U.S. Pat. No. No. 4,720,415 to Vander Wielen et al., issued Jan. 19, 1988, which is hereby incorporated by reference.

The term "stretch-to-stop" as used herein refers to a ratio determined from the difference between the unextended dimension of a composite elastic material and the maximum extended dimension of a composite elastic material upon the application of a specified tensioning force and dividing that difference by the unextended dimension of the composite elastic material. If the stretch-to-stop is expressed in percent, this ratio is multiplied by 100. For example, a composite elastic material having an unextended length of 5 inches and a maximum extended length of 10 inches upon applying a force of 2000 grams has a stretch-to-stop (at 2000 grams) of 100 percent. Stretch-to-stop may also be referred to as "maximum non-destructive elongation". Unless specified otherwise, stretch-to-stop values are reported herein at a load of 2000 grams. An exemplary method of measuring stretch-to-stop is given in Comparative Example 2.

As used herein, the term "nonwoven web" means a web having a structure of individual fibers or threads which are interlaid, but not in an identifiable, repeating manner. Nonwoven webs have been, in the past, formed by a variety of processes such as, for example, meltblowing processes, spunbonding processes and bonded carded web processes.

As used herein, the term "autogenous bonding" means bonding provided by fusion and/or self-adhesion of fibers and/or filaments without an applied external adhesive or bonding agent. Autogenous bonding may be provided by contact between fibers and/or filaments while at least a portion of the fibers and/or filaments are semi-molten or tacky. Autogenous bonding may also be provided by blending a tackifying resin with thermoplastic polymers used to form fibers and/or filaments. Fibers and/or filaments formed from such a blend can be adapted to self-bond with or without the application of pressure and/or heat. Solvents may also be used to cause fusion of fibers and filaments which remains after the solvent is removed.

As used herein, the term "meltblown fibers" means fibers formed by extruding a molten thermoplastic material through a plurality of fine, usually circular, die capillaries as molten threads or filaments into a high velocity gas (e.g. air) stream which attenuates the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, the disclosure of which is hereby incorporated by reference.

As used herein, the term "microfibers" means small diameter fibers having an average diameter not greater than about 100 microns, for example, having an average diameter of from about 0.5 microns to about 50 microns, or more particularly, microfibers may have an average diameter of from about 4 microns to about 40 microns.

As used herein, the term "spunbonded fibers" refers to small diameter fibers which are formed by extruding a molten thermoplastic material as filaments from a plurality of fine, usually circular, capillaries of a spinnerette with the diameter of the extruded filaments then being rapidly reduced as by, for example, eductive drawing or other well-known spun-bonding mechanisms. The production of spun-bonded nonwoven webs is illustrated in patents such as, for example, in U.S. Pat. No. 4,340,563 to Appel et al., and U.S. Pat. No. 3,692,618 to Dorschner et al. The disclosures of these patents are hereby incorporated by reference.

As used herein, the term "polymer" generally includes, but is not limited to, homopolymers, copolymers, such as, for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to, isotactic, syndiotactic and random symmetries.

As used herein, the term "superabsorbent" refers to absorbent materials capable of absorbing at least 10 grams of aqueous liquid (e.g. distilled water per gram of absorbent material while immersed in the liquid for 4 hours and holding substantially all of the absorbed liquid while under a compression force of up to about 1.5 psi.

As used herein, the term "consisting essentially of" does not exclude the presence of additional materials which do not significantly affect the desired characteristics of a given composition or product. Exemplary materials of this sort would include, without limitation, pigments, antioxidants, stabilizers, surfactants, waxes, flow promoters, particulates and materials added to enhance processability of the composition.

SUMMARY OF THE INVENTION

Problems associated with previous self-adhesive elastic nonwoven wraps and/or bandages have been addressed by the self-adhesive nonwoven elastic compressible composite material of the present invention.

The self-adhesive nonwoven elastic compressible composite material is composed of at least one elastic composite material and a coating of a self-adhesive material on at least a portion of at least one exterior surface of the elastic composite material so that the material is capable of being compressed in the Z-direction at least about 45 percent at a pressure of about 3 psi to a thickness of not less than about 0.035 inch. For example, the self-adhesive material may be capable of being compressed in the Z-direction at least about 55 percent at a pressure of about 3 psi to a thickness of not less than about 0.035 inch. As a further example, the self-adhesive material may be capable of being compressed in the Z-direction at least about 55 percent at a pressure of about 3 psi to a thickness of ranging from about 0.040 inch to about 0.2 inch. As yet another example, the self-adhesive material may be capable of being compressed in the Z-direction at least about 35 percent at a pressure of about 1 psi to a thickness of not less than about 0.035 inch. According to one aspect of the present invention, the composite elastic material may be composed of (1) at least one layer of an elastomeric nonwoven fibrous web; and (2) at least one layer of a relatively nonelastic gatherable material joined to the elastomeric nonwoven fibrous web at spaced-apart locations so that the gatherable material is gathered between the spaced-apart locations. Desirably, the peel strength of such a self-adhesive material is less than the peel strength which binds the layers of the elastic composite material. For example, the peel strength of the self-adhesive material may be at least about 5 percent less than the peel strength which binds the elastic composite material. As another example, the peel strength of the self-adhesive material may be from about 10 to about 98 percent less than the peel strength which binds the elastic composite material. As a further example, the peel strength of the self-adhesive material may be from about 20 to about 95 percent less than the peel strength which binds the elastic composite material. Desirably, the peel strength of the self-adhesive material will be from about 0.1 to about 1.0 pound per inch. For example, the peel strength of the self-adhesive material may be from about 0.3 to about 0.5 pound per inch. Desirably, the amount of force required to unwind a roll of the self-adhesive material will be from about 0.3 to about 2.0 pounds per inch. For example, the amount of force required to unwind a roll of the self-adhesive material may be from about 0.5 to about 1.2 pounds per inch.

According to the present invention, the coating of self-adhesive material may be located on gatherable material. In some embodiments, the coating of self-adhesive material may be located only on raised portions of the gathers present in the gatherable material. Where the composite material is composed on a layer of gatherable material and a layer of an elastomeric fibrous web, the coating of self-adhesive material can be located on elastomeric fibrous web The coating of self adhesive material may be in the form of a randomly scattered network of hot-melt adhesive filaments and/or fibers. The coating of self-adhesive material may be a coating of any suitable conventional commercially available hot-melt adhesive such as, for example, hot melt adhesives which may be based on blends of polyolefins, adhesive resins, and waxes.

According to the present invention, the gatherable layer can be a nonwoven web of fibers such as, for example, a web of spunbonded fibers, a web of meltblown fibers, a bonded carded web of fibers, a multi-layer material including at least one of the webs of spunbonded fibers, meltblown fibers, or a bonded carded web of fibers.

In one aspect of the present invention, the gatherable layer can be a composite material composed of a mixture of fibers and one or more other materials such as, for example, wood pulp, staple fibers, particulates or super-absorbent materials. Medicinal materials may be mixed with the fibrous materials.

The elastomeric nonwoven fibrous web component of the present invention is desirably a nonwoven web of elastomeric meltblown fibers which may include meltblown microfibers. In one aspect of the present invention, the elastomeric nonwoven web is a coherent stretchable sheet which can distribute tensioning forces across its width without creating pressure points or areas of concentrated tension. The elastic meltblown fibers may be an elastomeric polymer such as, for example, elastomeric polyesters, elastomeric polyurethanes, elastomeric polyamides, elastomeric copolymers of ethylene and at least one vinyl monomer, and elastomeric A-B-A' block copolymers wherein A and A' are the same or different thermoplastic polymer, and wherein B is an elastomeric polymer block. The elastomeric polymer may be blended with a processing aid.

In one aspect of the present invention, the elastic nonwoven fibrous web may be an anisotropic nonwoven fibrous web containing a substantially homogenous arrangement of meltblown fibers generally aligned along one of the planar dimensions of the web. The elastomeric meltblown fibers may also be a mixture of elastomeric meltblown fibers and one or more other materials such as, for example, wood pulp, staple-type fibers, particulates or super-absorbent materials. For example, the staple-type fibers may be polyester fibers, polyamide fibers, glass fibers, polyolefin fibers, cellulosic derived fibers, multi-component fibers, natural fibers, absorbent fibers, electrically conductive fibers or blends of two or more of said fibers. The particulate materials may be, for example, activated charcoal, clays, starches, and metal oxides.

According to one aspect of the present invention, self-adhesive composite material may have a basis weight ranging from about 40 to about 400 gsm. For example, the basis weight may range from about 100 to about 250 gsm.

According to another aspect of the present invention, there is provided a self-adhesive nonwoven composite elastic material composed of (1) at least one nonwoven web formed of elastomeric meltblown fibers; (2) at least one relatively nonelastic gatherable material formed of a mixture of fibers and one or more other materials such as, for example, wood pulp, staple-type fibers, particulates and super-absorbent materials, the gatherable material being joined to the elastomeric nonwoven fibrous web at spaced-apart locations so that the gatherable material is gathered between the spaced-apart locations; and (3) a coating of a self-adhesive material on at least a portion of at least one exterior surface of the composite elastic material.

In yet another aspect of the present invention, the self-adhesive composite elastic material is a product in the form of a wrap or bandage for use in human or veterinary medicine. In such a wrap or bandage, the self-adhesive composite elastic material may have a stretch-to-stop elongation of at least about 25 percent. For example, the stretch-to-stop elongation may range from about 35 to about 400 percent or more.

DETAILED DESCRIPTION OF THE INVENTION

Figure 1:
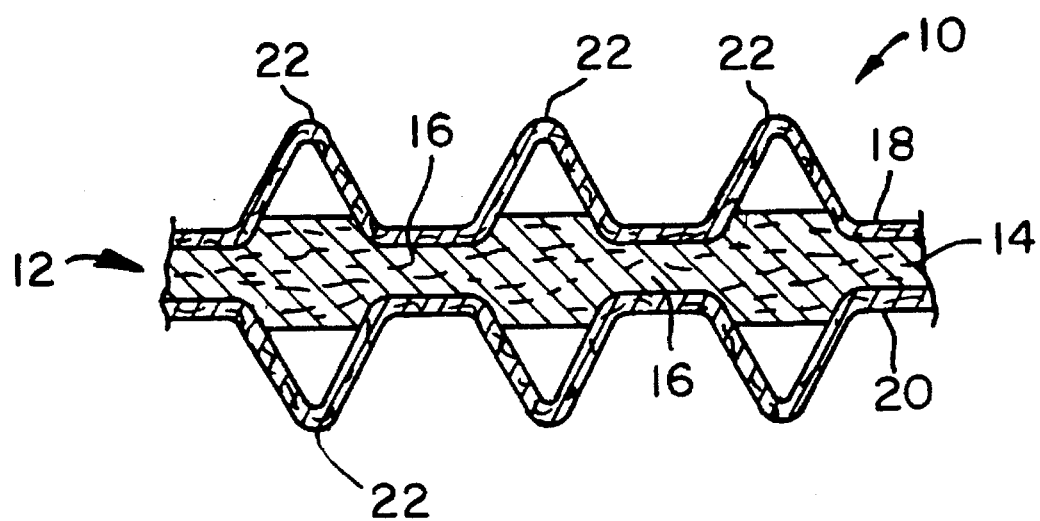
FIG. 1 is a view of an exemplary multilayer elastic composite compressible material.

The present invention provides a self-adhesive nonwoven elastic composite compressible material. According to the present invention, the self-adhesive nonwoven elastic composite material may be composed of at least one elastic composite material and a coating of a self-adhesive material on at least a portion of at least one exterior surface of the elastic composite material so that the material is capable of being compressed in the Z-direction at least about 45 percent at a pressure of about 3 psi to a thickness of not less than about 0.035 inch. The composite elastic material may be any suitable composite elastic material, elastic foam or the like. Desirably, the self-adhesive composite elastic material is a multilayer material having at least one elastic layer joined to at least one gatherable layer at least at two locations in which the gatherable layer is gathered between the locations where it is joined to the elastic layer. Generally speaking, the composite elastic material can be composed of (1) at least one elastomeric nonwoven fibrous web; and (2) at least one relatively nonelastic gatherable material joined to the elastomeric nonwoven fibrous web at spaced-apart locations so that the gatherable material is gathered between the spaced-apart locations.

Such a composite elastic material may be stretched to the extent that the nonelastic material gathered between the bond locations allows the elastic material to elongate. One type of a composite elastic material is referred to as a stretch-bonded laminate. Such a stretch-bonded laminate may be made as generally described, for example, in previously referenced U.S. Pat. No. 4,720,415 to Vander Wielen et al.

For example, an elastomeric nonwoven fibrous web can be unwound from a supply roll and passed through a nip of an S-roll arrangement. The elastomeric web may also be formed in-line and passed directly through the nip without first being stored on a supply roll.

Generally speaking, the elastic web can be passed through the nip of the S-roll arrangement in a reverse-S path. From the S-roll arrangement, the elastic web passes through the pressure nip formed by a bonder roller arrangement. Additional S-roll arrangements may be introduced between the S-roll arrangement and the bonder roller arrangement to stabilize the stretched material and to control the amount of stretching. Because the peripheral linear speed of the rollers of the S-roll arrangement is controlled to be less than the peripheral linear speed of the rollers of the bonder roller arrangement, the elastic web is tensioned between the S-roll arrangement and the pressure nip of the bonder roll arrangement. By adjusting the difference in the speeds of the rollers, the elastic web is tensioned so that it stretches a desired amount and is maintained in such stretched condition Simultaneously, a first and second gatherable layer is unwound from a supply roll and passed through the nip of the bonder roller arrangement. It is contemplated that the first gatherable layer and/or the second gatherable layer may be formed in-line by extrusion processes such as, for example, meltblowing processes, spunbonding processes or film extrusion processes and passed directly through the nip without first being stored on a supply roll.

The first gatherable layer and second gatherable layer are joined to the elastic web (while the web is maintained in its elongated condition) during their passage through the bonder roller arrangement to form a composite elastic material (i.e., a stretch-bonded laminate). The stretch-bonded laminate is immediately relaxed upon release of the tensioning force provided by the S-roll arrangement and the bonder roll arrangement, whereby the first gatherable layer and the second gatherable layer are gathered in the stretch-bonded laminate. The stretch-bonded laminate is then wound up on a winder. Referring to FIG. 1, there is illustrated (schematically and not necessarily to scale, including relative thicknesses of the layers and size of embossed areas) an exemplary composite elastomeric material having a stretch-bonded laminate structure at 10. The composite elastomeric material 12 contains an elastomeric nonwoven fibrous web 14 joined at spaced-apart locations 16 to a first gatherable layer of material 18 and a second gatherable layer of material 20 so that the gatherable layers form gathers 22 between the spaced-apart locations 16. Generally speaking, the elastomeric composite material can be made to stretch and recover in only a single direction or it can be made to stretch and recover in at least two directions. For most purposes, stretch and recovery in a single direction is adequate. An exemplary elastomeric composite material that can stretch and recover in two directions may be made as generally described in U.S. Pat. No. 5,116,662 to Morman, issued May 26, 1992. That patent is also commonly assigned to the assignee of the present application. The contents of that patent are hereby incorporated by reference.

Generally speaking, a desirable feature of stretch-bonded laminate materials created by joining a first gatherable layer of material 18 and a second gatherable layer of material 20 to a nonwoven fibrous web 14 in such a manner that the gatherable layers form gathers 22 between the spaced-apart locations 16 may produce a material that has useful levels of Z-direction compressibility (i.e., compressibility in the thickness direction) which may provide desirable levels of softness and comfort.

Desirably, the elastic composite material should be capable of being compressed in the Z-direction at least about 35 percent at a pressure of about 1 psi to a thickness of not less than about 0.035 inch. For example, the elastic composite material may be capable of being compressed in the Z-direction at least about 55 percent at a pressure of about 3 psi to a thickness of not less than about 0.035 inch. As a further example, elastic composite material may be capable of being compressed in the Z-direction at least about 55 percent at a pressure of about 3 psi to a thickness of ranging from about 0.040 inch to about 0.2 inch.

The coating of a self-adhesive material is added to at least a portion of at least one exterior surface of the elastic composite material so that the peel strength of the self-adhesive material is less than the peel strength of the layers which bind the elastic composite material. It is very desirable that the peel strength of the self-adhesive material be less than the peel strength which binds the elastic composite material to prevent delamination (i.e., separation of the layers) of the elastic composite material.

For example, the peel strength of the self-adhesive material may be at least about 5 percent less than the peel strength which binds the elastic composite material. As another example, the peel strength of the self-adhesive material may be from about 10 to about 98 percent less than the peel strength which binds the elastic composite material. As a further example, the peel strength of the self-adhesive material may be from about 20 to about 95 percent less than the peel strength which binds the elastic composite material. Desirably, the peel strength of the self-adhesive material will be from about 0.1 to about 1.0 pound per inch. For example, the peel strength of the self-adhesive material may be from about 0.3 to about 0.5 pound per inch. Desirably, the amount of force required to unwind a roll of the self-adhesive material will be from about 0.3 to about 2.0 pounds per inch. For example, the amount of force required to unwind a roll of the self-adhesive material may be from about 0.5 to about 1.2 pounds per inch.

The coating of self-adhesive material may be located on the gatherable material. In some embodiments, the coating of self-adhesive material may be located only on raised portions of the gathers present in the gatherable material. Where the composite material is composed on a layer of gatherable material and a layer of an elastomeric fibrous web, the coating of self-adhesive material can be located on the elastomeric fibrous web While it is contemplated that the self-adhesive material may be an organic solvent based adhesive or water based adhesive (e.g., latex adhesive) that can be printed, brushed or sprayed onto the elastic composite material, it is desirable that the coating of self adhesive material be in the form of a randomly scattered network of hot-melt adhesive filaments and/or fibers produced by conventional hot-melt adhesive spray equipment. The coating of hot-melt self-adhesive material may also desirably be applied in patterns such as, for example, semi-cycloidal patterns. For example, a self-adhesive material such as a hot-melt self adhesive material may be applied to a composite elastic material as generally described by U.S. Pat. No. 4,949,668 to Heindel, et al., issued Aug. 21, 1990, which is hereby incorporated by reference. Desirably, the hot-melt adhesive coating should be applied while the stretch-bonded laminate material is under a relatively small amount of tension. For example, the hot-melt adhesive coating can be applied while the stretch-bonded laminate material is under only enough tension needed to have the material travel through the adhesive application process.

The coating of self-adhesive material may be a coating of any suitable conventional commercially available hot-melt adhesive such as, for example, hot melt adhesives which may contain a blend of thermoplastic polymers (e.g., thermoplastic polyolefins), adhesive resins, and waxes.

Exemplary hot-melt self-adhesive materials which may be used include auto-adhesive 6631-117-1 and auto-adhesive 6631-114-4 available from the National Starch & Chemical Company, Adhesives Division, Bridgewater, N.J. Other self-adhesive materials may be, for example, Hot Melt Adhesive H-9140 available from Findley Adhesives, Incorporated, Wauwatosa, Wis. These self-adhesive materials may be blended with other materials such as, for example antioxidants, stabilizers, surfactants, flow promoters, particulates and materials added to enhance processability of the composition.

Generally speaking, the gatherable layer can be a nonwoven web of fibers such as, for example, a web of spunbonded fibers, a web of meltblown fibers, a bonded carded web of fibers, a multi-layer material including at least one of the webs of spunbonded fibers, meltblown fibers, or bonded carded web of fibers. Any suitable non-elastomeric fiber forming resins or blends containing the same may be utilized to form the nonwoven gatherable layer of material. For example, such polymers include polyolefins, non-elastomeric polyesters, non-elastomeric polyamides, cellulosic derived polymers, vinyl chlorides and polyvinyl alcohols.

The gatherable layer can be a composite material composed of a substantially homogenous mixture of meltblown fibers and other fibrous materials and/or particulates. For an example of such a mixture, reference is made to U.S. Pat. No. 4,209,563, incorporated herein by reference, in which meltblown fibers and other fibrous materials are commingled to form a single coherent web of randomly dispersed fibers. Another example of such a composite web would be one made by a technique such as disclosed in previously referenced U.S. Pat. No. 4,741,949. That patent discloses a nonwoven material which includes a mixture of meltblown thermoplastic fibers and other materials. The fibers and other materials are combined in the gas stream in which the meltblown fibers are borne so that an intimate entangled commingling of meltblown fibers and other materials, e.g., wood pulp, staple fibers or particulates such as, for example, activated charcoal, clays, starches, or hydrocolloid (hydrogel) particulates commonly referred to as super-absorbents occurs prior to collection of the fibers upon a collecting device to form a coherent web of randomly dispersed fibers.

Accordingly, it is contemplated that a self-adhesive nonwoven composite elastic material may be composed of (1) at least one elastomeric nonwoven fibrous web; (2) at least one relatively nonelastic gatherable material composed of a mixture of meltblown fibers and one or more other materials such as, for example, wood pulp, staple-type fibers, particulates and super-absorbent materials, the gatherable material being joined to the elastomeric nonwoven fibrous web at spaced-apart locations so that the gatherable material is gathered between the spaced-apart locations; and (3) a coating of a self-adhesive material on at least a portion of at least one exterior surface of the composite elastic material.

The elastomeric nonwoven fibrous web component of the present invention is desirably a nonwoven web of elastomeric meltblown fibers which may include meltblown microfibers. The elastomeric nonwoven fibrous web may be formed utilizing one or more conventional meltblowing die arrangements. The meltblowing die arrangements may be arranged in series and/or may be alternated with one or more conventional meltblowing apparatus or web-forming means. Several dies for forming meltblown fibers may also be arranged in series to provide superposed layers of fibers. It is also contemplated that an anisotropic nonwoven fibrous web may be formed directly upon at least one layer of a material such as, for example, a nonwoven fabric, a knit fabric, woven fabric and/or film.

Generally, any suitable elastomeric fiber forming resins or blends containing the same may be utilized for the elastomeric meltblown fibers. The fibers may be formed from the same or different elastomeric resin.

For example, the elastomeric meltblown fibers may be made from elastomeric block copolymers. Exemplary elastomeric block copolymers may have the general formula A-B-A' where A and A' are each a thermoplastic polymer endblock which contains a styrenic moiety such as a poly (vinyl arene) and where B is an elastomeric polymer midblock such as a conjugated diene or a lower alkene polymer. The block copolymers may be, for example, (polystyrene/poly(ethylene-butylene)/polystyrene) block copolymers available from the Shell Chemical Company under the trademark KRATON® G. One such block copolymer may be, for example, KRATON® G-1657.

Other exemplary elastomeric materials which may be used include polyurethane elastomeric materials such as, for example, those available under the trademark ESTANE from B. F. Goodrich & Co., polyamide elastomeric materials such as, for example, those available under the trademark PEBAX from the Rilsan Company, and polyester elastomeric materials such as, for example, those available under the trade designation Hytrel from E. I. DuPont De Nemours & Company. Formation of elastomeric meltblown fibers from polyester elastic materials is disclosed in, for example, U.S. Pat. No. 4,741,949 to Morman et al., hereby incorporated by reference. Useful elastomeric polymers also include, for example, elastic copolymers of ethylene and at least one vinyl monomer such as, for example, vinyl acetates, unsaturated aliphatic monocarboxylic acids, and esters of such monocarboxylic acids. The elastic copolymers and formation of elastomeric meltblown fibers from those elastic copolymers are disclosed in, for example, U.S. Pat. No. 4,803,117 to Daponte, hereby incorporated by reference.

Processing aids may be added to the elastomeric polymer. For example, a polyolefin may be blended with the elastomeric polymer (e.g., the elastomeric block copolymer) to improve the processability of the composition. The polyolefin must be one which, when so blended and subjected to an appropriate combination of elevated pressure and elevated temperature conditions, is extrudable, in blended form, with the elastomeric polymer. Useful blending polyolefin materials include, for example, polyethylene, polypropylene and polybutene, including ethylene copolymers, propylene copolymers and butene copolymers. A particularly useful polyethylene may be obtained from the U.S.I. Chemical Company under the trade designation Petrothene NA 601 (also referred to herein as PE NA 601 or polyethylene NA 601). Two or more of the polyolefins may be utilized.

Extrudable blends of elastomeric polymers and polyolefins are disclosed in, for example, previously referenced U.S. Pat. No. 4,663,220.

Desirably, the elastomeric meltblown fibers should have some tackiness or adhesiveness to enhance autogenous bonding. For example, the elastomeric polymer itself may be tacky when formed into fibers or, alternatively, a compatible tackifying resin may be added to the extrudable elastomeric compositions described above to provide tackified elastomeric fibers that autogenously bond. In regard to the tackifying resins and tackified extrudable elastomeric compositions, note the resins and compositions as disclosed in U.S. Pat. No. 4,787,699, hereby incorporated by reference.

Any tackifier resin can be used which is compatible with the elastomeric polymer and can withstand the high processing (e.g., extrusion) temperatures. If the elastomeric polymer (e.g., elastomeric block copolymer) is blended with processing aids such as, for example, polyolefins or extending oils, the tackifier resin should also be compatible with those processing aids. Generally, hydrogenated hydrocarbon resins are preferred tackifying resins, because of their better temperature stability. REGALREZ™ and ARKON™ P series tackifiers are examples of hydrogenated hydrocarbon resins. ZONATAK™501 lite tackifer resin is an example of a terpene hydrocarbon. REGALREZ™ hydrocarbon resins are available from Hercules Incorporated. ARKON™ P series resins are available from Arakawa Chemical (U.S.A.) Incorporated. Of course, the present invention is not limited to use of such three tackifying resins, and other tackifying resins which are compatible with the other components of the composition and can withstand the high processing temperatures, can also be used.

Typically, the blend used to form the elastomeric fibers include, for example, from about 40 to about 80 percent by weight elastomeric polymer, from about 5 to about 40 percent polyolefin and from about 5 to about 40 percent resin tackifier. For example, a particularly useful composition included, by weight, about 61 to about 65 percent KRATON™ G-1657, elastomer about 17 to about 23 percent polyethylene NA 601, and about 15 to about 20 percent REGALREZ™ 1126 tackifying resin.

As discussed above for the gatherable layer, the elastomeric nonwoven web may also include a substantially homogenous mixture of meltblown fibers and other fibrous materials and/or particulates. Exemplary materials and processes are disclosed in previously referenced U.S. Pat. Nos. 4,209,563 and 4,741,949.

The elastic nonwoven fibrous web may be an anisotropic nonwoven fibrous web containing a substantially homogenous arrangement of meltblown fibers generally aligned along one of the planar dimensions of the web such as, for example, the machine direction. Such an anisotropic nonwoven fibrous web would be desirable where the elastic component of the self-adhesive composite elastic material does not need the same stretch and recovery properties in every direction. If the elastic component is designed to have the required stretch and recovery properties in only the direction that the gatherable material allows the laminate to stretch, then relatively less elastomeric material could be used than if the web was isotropic. Since elastomeric materials generally tend to be quite expensive, reducing the amount of elastomeric material while still achieving the desired physical properties could be accomplished. Such an anisotropic elastic fibrous web may be made as generally described, for example, by U.S. Pat. No. 5,366,793, filed on Apr. 7, 1992, by Fitts, et al., which is hereby incorporated by reference.

Generally speaking, the self-adhesive composite material may have a basis weight ranging from about 10 to about 400 gsm. For example, the self-adhesive composite material may have a basis weight ranging from about 40 to about 400 gsm. As a further example, the basis weight may range from about 100 to about 250 gsm. The self-adhesive composite elastic material may be utilized as a self-adhesive product such as a wrap or bandage. Such wraps or bandages have wide application in human or veterinary medicine. When used as a wrap or bandage, the self-adhesive composite elastic material may have a stretch to stop elongation within a range that permits the wrap or bandage to be applied at an appropriate level of tension for the intended use. For example, the self-adhesive product may be composed of a composite elastic material that has a stretch-to-stop elongation of at least about 25 percent. As a further example, the self-adhesive product may be composed of a composite elastic material that has a stretch-to-stop elongation ranging from about 35 percent to about 400 percent.

EXAMPLES

Nonwoven Elastomeric Fibrous Web

The nonwoven elastomeric fibrous web was a nonwoven web of elastomeric meltblown fibers formed from an elastomeric composition which contained about 63 percent, by weight, KRATON™ G-1657, elastomer about 17 percent, by weight, polyethylene NA 601, and about 20 percent, by weight, REGALREZ™ 1126 tackifying resin. The elastomeric nonwoven webs of meltblown fibers were formed utilizing conventional meltblowing processes in multiple banks to produce a nonwoven elastomeric fibrous web having a basis weight of about 70 gsm.

Stretch-bonded Laminate

Several composite elastomeric materials referred to as stretch-bonded laminates were made utilizing the nonwoven elastomeric fibrous web described above.

Generally speaking, the elastomeric nonwoven fibrous webs (i.e., webs of meltblown fibers) were carried by the forming surface at a specified rate, lifted off the forming surface by a pick-off roll moving at a faster rate and then drawn to a specified calender/forming surface draw ratio to achieve a desired level of elongation. At this elongation the drawn elastomeric nonwoven web of meltblown fibers was fed into a calender roller along with upper and lower non-elastic web facings. Each facing was a conventional polypropylene spunbonded continuous filament web having a basis weight of about 0.4 ounces per square yard (about 14 gsm) which was joined to the elastomeric nonwoven web of meltblown fibers at spaced apart locations to form a stretch-bonded laminate structure. The stretched-bonded laminate was relaxed as it exited the nip so that gathers and puckers would form in the gatherable material and the elastomeric component contracted to generally about its pre-stretched dimensions. The laminate was wound onto a driven wind-up roll under slight tension.

Self-Adhesive Elastic Composite Material

The stretch-bonded laminate described above having a basis weight of about 100 gsm was passed under a melt-spray apparatus which extruded a fine spray of hot-melt adhesive. The stretch-bonded laminate was in its relaxed (i.e., unstretched) condition as the hot-melt adhesive was applied. The melt-spray equipment was a conventional melt-blowing die tip having a 10 inch slot and 20 holes per inch flush with the slot. The adhesive was sprayed at a forming distance of 1½ inches from the surface of the stretch-bonded laminate resulting in a spray pattern of about 10½ inch width.

EXAMPLE 1

A hot-melt adhesive obtained from the National Starch & Chemical Company, Adhesives Division under the trade designation National 70-3828 was processed at the following machine conditions:
Pre-Melt Temp.=260° F.
Main Melt Temp.=275° F.
Hose Temp.=280° F.
Die Temp.=300° F.
Air Temp.=450° F. @ 20 psi
Forming Dist.=1½ inches At these conditions, it was estimated that the temperature of the adhesive coming out of die ranged from about 275° to about 285° F.

Running at a machine speed of 100 fpm (feet per minute), the adhesive add-on was calculated to be 5 grams per square meter (gsm). A rubber-coated nip roll was covered with a sleeve of release paper, allowing the stretch-bonded laminate to be processed without a layer of release paper as it was sprayed and wound. After spray coating one side on the first stretch-bonded laminate, the adhesion properties of the coated stretch-bonded laminate were checked and it was found that the adhesive could be peeled off the surface of the stretch-bonded laminate.

EXAMPLE 2

A hot melt adhesive obtained from the Findley Adhesives Company under the trade designation Findley H-9140 was processed at the following machine conditions:
Pre-Melt Temp.=330° F.
Main Melt Temp.=335° F.
Hose Temp.=335° F.
Die Temp.=340° F.
Air Temp.=450° F. @ 20 psi
Forming Dist.=1½ inches It was noted that this adhesive required higher processing conditions. The first roll was run at a line speed of 100 fpm to obtain a 5 gsm adhesive add-on level. The roll was run back through and spray coated on the opposite side to generate stretch-bonded laminate with 5 gsm adhesive add-on per side. This material showed no adhesive pulling off the stretch-bonded laminate surface.

Coating level, air temperature, air pressure, and adhesive temperature were varied to produce the desired level of adhesive add-on. It was necessary to use release paper to prevent adhesive buildup on the equipment.

EXAMPLE 3

A hot melt adhesive was obtained from the Findley Adhesives Company under the trade designation Findley H9078-01. It was found that the melt-spray equipment operated most effectively when this particular adhesive was heated to a level where its viscosity was about 4000 centipoise. The following machine settings were used to achieve a desirable level of viscosity:
Adhesive Running Temp.=300° F.
Forming Distance=1½ inches
Line Speed=250 ft./min.

The stretch-bonded laminate was coated on two sides at about 4 mg/in.$^2$ loading. A polypropylene spunbond continuous filament facing material (basis weight 0.4 oz/yd$^2$ (14 gsm)) was also coated. However, it was only coated on one side. The Findley H9078-01 hot-melt adhesive appeared to have a good level of tack to itself but too much adherence to surfaces such as skin. The adhesive was so strong that the spunbonded polypropylene and elastomeric nonwoven fibrous web layers of the stretch-bonded laminate separated when the self-adhesive performance of the material was examined.

EXAMPLE 4

A hot-melt adhesive was obtained from the National Starch & Chemical Company, Adhesives Division under the trade designation National 70-3842. Because this particular hot-melt adhesive had a much higher viscosity than many of the other adhesives, the following machine settings were chosen:
Adhesive Running Temp.=360° F.
Forming Distance =1½ inches
Line Speed=250 ft./min.

This adhesive was also added to each side at a loading of about 4 milligrams per square inch (mg/in.$^2$). The coated material had a rubbery feel from this adhesive, which felt similar to latex saturated products. It was observed that when two layers of stretch-bonded laminate coated with the National 70-3842 hot-melt adhesive were pulled apart, the adhesive came off the stretch-bonded laminate surfaces in long, stringy segments.

EXAMPLE 5

A hot melt adhesive obtained from the Findley Adhesives Company under the trade designation Findley H-9054-01 was processed at the following machine conditions:
Adhesive Running Temp.=310° F.
Forming Distance =1½ inches
Line Speed=250 ft./min.

This adhesive processed much like the adhesive of Example 3 (i.e, Findley adhesive H-9078-01). However, the material did not feel very tacky at all. In addition, the material did not appear to have a high level of self-adhesion.

Comparative Examples

The following comparative examples illustrate a process in which a self-adhesive coating is applied to a spunbonded gatherable web before the web was joined to the elastic nonwoven fibrous web to create a stretch-bonded laminate material. The examples illustrate that such self-adhesive coated spunbonded gatherable webs may be utilized to make stretch-bonded laminate materials having useful stretch-to-stop elongations.

Control Material

A nonwoven elastomeric fibrous web of elastomeric meltblown fibers was formed from an elastomeric composition which contained about 63 percent, by weight, KRATON™ G-1657 elastomer, about 17 percent, by weight, polyethylene NA 601, and about 20 percent, by weight, REGALREZ™ 1126 tackifying resin. The elastomeric meltblown fibers were formed utilizing conventional meltblowing processes in multiple banks to produce a nonwoven elastomeric fibrous web having a basis weight of about 112 gsm.

The elastomeric nonwoven fibrous web was elongated and joined to upper and lower non-elastic web facings at spaced apart locations according to the process described above to make a stretch-bonded laminate. Each facing was a conventional polypropylene spunbond web having a basis weight 0.4 ounces per square yard (about 14 gsm). The stretched-bonded laminate was relaxed as it exited the nip so that gathers and puckers would form in the gatherable material and the elastomeric component contracted to generally about its pre-stretched dimensions. The laminate was wound onto a driven wind-up roll under slight tension. Samples of material made in this manner were identified as "Control" materials.

Comparative Example 1

A hot melt adhesive obtained from the Findley Adhesives Company under the trade designation Findley H-9078 was coated onto a 14 gsm web of spunbonded polypropylene as set forth in Example 3. The self-adhesive coated spunbonded polypropylene web was introduced into the stretch-bonded laminate converting process described above. When the self-adhesive coated spunbonded material was joined to an elongated elastic nonwoven fibrous web using thermal bonding techniques, the spunbonded material became very sticky and tended to break off in the bonding nip, winding itself around the anvil roll. There was considerable adhesive build-up on both calendar rolls, even at the low bonding temperatures. A small amount of a stretch-bonded material was produced.

Comparative Example 2

A hot melt adhesive obtained from the Findley Adhesives Company under the trade designation Findley H-9054 was coated onto a 14 gsm web of spunbonded polypropylene as set forth in Example 5. When introduced into the stretch-bonded laminate converting process described above to join the self-adhesive coated spunbonded material to an elongated elastic nonwoven fibrous web, the spunbonded material did not stick as badly to the nip as the material of Comparative Example 1. However, the adhesive did affect the recovery rate, which caused the material to wrap itself around the calendar roll. A small amount of a stretch-bonded material was produced.

Figure 2:
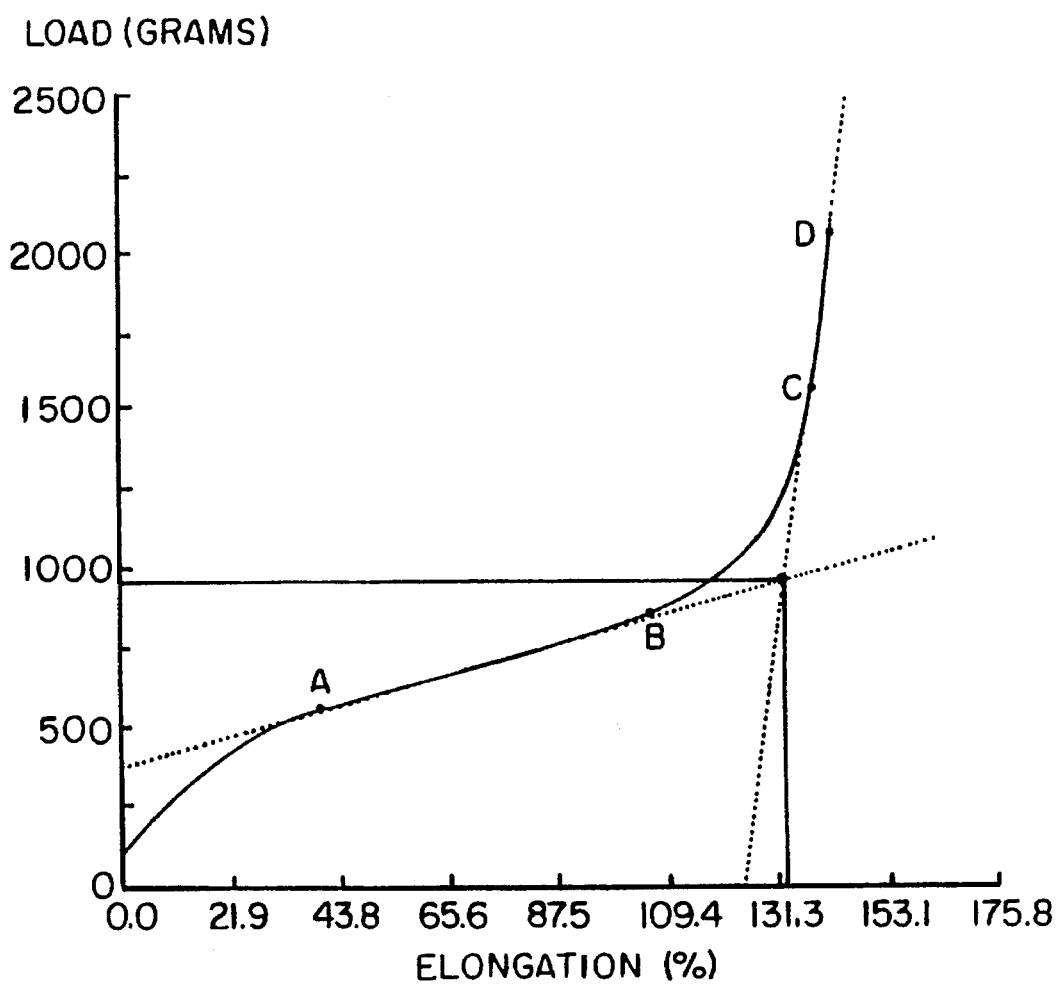
FIG. 2 is a graph of load versus elongation determined during tensile testing of an exemplary elastic composite compressible material.

The stretch-to-stop elongations of the stretch-bonded-laminates was measured for each sample. Data from tensile tests (i.e., measurements of load and elongation) conducted on the Instron Model 1122 Universal Test Equipment was used to generate load versus elongation curves for each stretch-bonded laminate sample. FIG. 2 is a representation of an exemplary load versus elongation curve for the initial elongation of a stretch bonded laminate to a maximum applied load of 2000 grams. As can be seen from the graph, the slope of the line tangent to the curve between points A and B represents the general elongation versus load characteristics provided primarily by the elastic component of the stretch bonded laminate.

The slope of the load versus elongation curve increases substantially once the stretch-bonded laminate has been fully extended to eliminate the gathers or puckers in the laminate. This region of substantial increase in slope occurs at about the laminate's stretch-to-stop elongation. The slope of the line tangent to the curve between points C and D after this region represents the general elongation versus load characteristics provided primarily by the non-elastic component (i.e., the gatherable web) of the stretch-bonded laminate.

The intersection of the lines passing through A-B and C-D is referred to as the point of intercept. The stretch-to-stop elongation is approximately the elongation at the point of intercept (i.e., elongation at intercept).

Results of stretch-to-stop testing are as follows for the comparative examples described above:
   Control—No Adhesive=140%
   Findley H907=110%
   Findley H9054=100%

TENSILE TESTING OF SELF-ADHESIVE
ELASTIC MATERIALS

The following examples describe measurements of tensile properties of three self-adhesive elastic materials. Two of the materials are VETRAP® and EQUISPORT™ self-adhesive wrapping materials, available from the Minnesota Mining and Manufacturing Company. The other material is a self-adhesive elastic composite material formed from a stretch bonded laminate material composed of a elastic nonwoven web of meltblown fibers joined to spunbonded polypropylene continuous filaments. Specific details of that material are described below.

All three materials were tested under the same conditions utilizing an Instron Model 1122 Universal Test Instrument equipped with Instron Series IX automation software.

Self-Adhesive Stretch-Bonded Laminate

A nonwoven web of elastomeric meltblown fibers was formed from an elastomeric composition which contained about 63 percent, by weight, KRATON™ G-1657 elastomer, about 17 percent, by weight, polyethylene NA 601, and about 20 percent, by weight, REGALREZ™ 1126 tackifying resin. The elastomeric nonwoven web of meltblown fibers was formed utilizing conventional meltblowing processes in multiple banks to produce a nonwoven elastomeric fibrous web having a basis weight of about 94 gsm.

Several composite elastomeric materials referred to as stretch-bonded laminates were made utilizing the nonwoven elastomeric fibrous web described above. The elastomeric nonwoven fibrous web was elongated and joined to upper and lower non-elastic web facings at spaced apart locations according to the process described above to make a stretch-bonded laminate. Each facing was a conventional polypropylene spunbond web having a basis weight 0.4 ounces per square yard (about 14 gsm). The stretched-bonded laminate was relaxed as it exited the nip so that gathers and puckers formed in the gatherable material and the elastomeric component contracted to generally about its pre-stretched dimensions.

The material was spray coated on both sides with a hot melt adhesive obtained from the Findley Adhesives Company under the trade designation Findley H-9140 essentially in accordance with Example 2 above.

Stretch-To-Stop Elongation

Stretch-to-stop elongations were determined for each sample utilizing the Instron test equipment as described above. Stretch-to-stop (STS) was about 130 percent for the self-adhesive stretch-bonded laminate (i.e., cohesive SBL). Stretch-to-stop (STS) measured for VETRAP® self-adhesive wrapping material was about 100 percent, and stretch-to-stop (STS) measured for EQUISPORT™ self-adhesive wrapping material was about 140 percent.

T-Peel Testing

Sample materials were cut to one inch by nine inch strips and backed with adhesive tape available from Minnesota Mining and Manufacturing Company under the trade designation 3M 3650-G Tape. They were then placed together with "sticky" sides together and joined by rolling a five pound roller back and forth over the sample about ten times. The samples were mounted on the Instron test equipment and measured under the following conditions:
   Crosshead Speed: 10 in./min.
   Gauge Length: 1 inch
   Grip Distance: 1 inch
   Sample Dimensions: 1 in. by 9 in.

Sample Type: ASTM D 1876-72 (reapproved 1983)
Jaw Size: Both 1 in. by 1 in.
The following data was generated from these tests:

TABLE 1

T-PEEL RESISTANCE OF
SELF-ADHESIVE MATERIALS

| Material | Average Load (grams) | | | | | |
|---|---|---|---|---|---|---|
| | 0–2 in. | 2–4 in. | 4–6 in. | 6–8 in. | 8–10 in. | AVG. |
| COHESIVE SBL | 8.30 | 11.65 | 11.12 | 9.46 | 9.21 | 9.95 |
| VETRAP ® | 90.11 | 92.90 | 79.74 | 79.00 | 76.25 | 83.60 |
| EQUISPORT ™ | 79.15 | 84.34 | 84.29 | 84.39 | 83.09 | 83.05 |

Adhesive Shear Strength

Samples for this test cut into two inch by six inch strips and backed with 3M 3650-G tape. They were then attached to one another, "sticky" sides together, with four square inches of contact area. The samples were mounted on the Instron test equipment and the pulled vertically by the Instron under the following conditions:
  Crosshead Speed: 10 in./min.
  Gauge Length: 3 inches
  Grip Distance: 3 inches
  Sample Dimensions: 2 in. by 6 in.
  Jaw Size: Both 3 in. by 1 in.
The following data was generated from these tests:

TABLE 2

SHEAR TESTING OF SELF-ADHESIVE MATERIALS

| Material | Average Maximum Load (grams) |
|---|---|
| COHESIVE SBL | 1318 |
| VETRAP ® | 5466 |
| EQUISPORT ™ | 11400 |

Tensile Strength at 50% Gauge Length and 50% Stretch-To-Stop Elongation

For these tests, samples were cut into four inch by six inch rectangles (the six inch length in the material's machine direction). Each sample was mounted on the Instron test equipment and pulled to break under the following conditions:

Crosshead Speed: 12 in./min.
  Gauge Length: 3 inches
  Grip Distance: 3 inches
  Sample Dimensions: 4 in. by 6 in.
  Sample Type: ASTM D 4964-89
  Jaw Size: Both 3 in. by 1 in.

The COHESIVE SBL, VETRAP® wrap, and EQUISPORT™ wrap samples each had slightly different stretch-to-stop elongations. This did not affect determination of load at 50 percent gauge length. This load was measured at a crosshead travel of about 1.5 inches. The load at 50 percent stretch-to-stop elongation was determined at 50 percent of the available crosshead travel according to the stretch-to-stop elongations reported above.

TABLE 3

TENSILE STRENGTH OF
SELF-ADHESIVE MATERIALS

| Material | STS (%) | Load at 50% Gauge Length (g) | Load at 50% STS Elongation (g) |
|---|---|---|---|
| COHESIVE SBL | 130 | 824.40 | 979.30 |
| VETRAP ® | 100 | 417.50 | 417.50 |
| EQUISPORT ™ | 140 | 964.40 | 1246.00 |

Relaxation Testing of Self-Adhesive Materials at 102° F.

Measurements of thermal relaxation were conducted utilizing the Instron test equipment. The test jaws were surrounded by an Instron Model 3111 series 808 environmental chamber (which had a window in the door) during the tests so the sample environment (temperature) could be controlled. The environmental chamber was preset to a desired temperature and allowed to come to equilibrium. A thermometer was used to insure an accurate temperature reading. Test samples for relaxation testing were cut to four inches by six inches, mounted in the jaws of the Instron test instrument and stretched to 50 percent of their stretch-to-stop elongation (stretch-to-stop is 130 percent for Cohesive SBL, 100 percent for VETRAP® wrap, and 140 percent for EQUISPORT™ wrap). Samples were held for 30 minutes at 50 percent of their stretch-to-stop elongation in the Environmental Chamber maintained at a temperature of 102° F. (38.8° C.). Samples were stretched under the following conditions:
  Crosshead Speed: 10 in./min.
  Gauge Length: 4 inches
  Grip Distance: 4 inches
  Sample Dimensions: 4 in. by 6 in.
  Sample Type: ASTM 4964-89
  Jaw Size: 4 in. by 1.5 in. (Chamber Jaws)
The following data was generated from these tests:

TABLE 4

RELAXATION AFTER 30 MINUTES –102° F.
SELF-ADHESIVE MATERIALS

| Material | Peak Load (grams) | Load After 30 Minutes (grams) | Total Energy Absrpt. (g/in) | Delta Load (grams) | Percent Relaxation (%) |
|---|---|---|---|---|---|
| COHESIVE SBL | 699.10 | 314.80 | 6943 | 384.3 | 55.54 |
| VETRAP ® | 368.30 | 274.80 | 5366 | 93.4 | 25.36 |
| EQUISPORT ™ | 1110.00 | 878.50 | 16770 | 231.2 | 20.80 |

Simulated Aging Study

For these tests, a test matrix was set up to determine the effect of a prolonged exposure to a heated environment. Three different temperatures and three different intervals of time were selected. The study was designed to simulate prolonged exposure to temperatures of about 200° F., 150° F. and 100° F. Samples were exposed to those temperatures for three different time intervals: 6 hours, 24 hours, and one week. The samples were held at the test temperatures in Fischer Isotemp® Model 282 Vacuum ovens. Each sample was allowed to cool for 24 hours before being mounted on the Instron test equipment and pulled to break under the following conditions:

Crosshead Speed: 12 in./min.
Gauge Length: 3 inches
Grip Distance: 3 inches
Sample Dimensions: 4 in. by 6 in.
Sample Type: ASTM 4964-89
Jaw Size: Both 3 in. by 1 in.

The following tables show the average data generated from these tests:

TABLE 5

SELF-ADHESIVE MATERIALS
AGED 6 HOURS AT 102.2° F.

| Material | STS (%) | Load at 50% Gauge Length (g) | Load at 50% STS Elongation (g) |
|---|---|---|---|
| COHESIVE SBL | 130 | 877.3 | 1030.0 |
| VETRAP ® | 100 | 363.0 | 363.0 |
| EQUISPORT ™ | 140 | 1025.0 | 1364.0 |

TABLE 6

SELF-ADHESIVE MATERIALS
AGED 24 HOURS AT 102.2° F.

| Material | STS (%) | Load at 50% Gauge Length (g) | Load at 50% STS Elongation (g) |
|---|---|---|---|
| COHESIVE SBL | 130 | 779.7 | 930.9 |
| VETRAP ® | 100 | 390.4 | 390.4 |
| EQUISPORT ™ | 140 | 999.8 | 1361.0 |

TABLE 7

SELF-ADHESIVE MATERIALS
AGED 1 WEEK AT 102.2° F.

| Material | STS (%) | Load at 50% Gauge Length (g) | Load at 50% STS Elongation (g) |
|---|---|---|---|
| COHESIVE SBL | 130 | 802.8 | 946.0 |
| VETRAP ® | 100 | 356.0 | 356.0 |
| EQUISPORT ™ | 140 | 1015.0> | 1337.0 |

TABLE 8

SELF-ADHESIVE MATERIALS
AGED 6 HOURS AT 147.6° F.

| Material | STS (%) | Load at 50% Gauge Length (g) | Load at 50% STS Elongation (g) |
|---|---|---|---|
| COHESIVE SBL | 130 | 829.0 | 973.7 |
| VETRAP ® | 100 | 374.9 | 374.0 |
| EQUISPORT ™ | 140 | 965.1 | 1244.0 |

TABLE 9

SELF-ADHESIVE MATERIALS
AGED 24 HOURS AT 147.6° F.

| Material | STS (%) | Load at 50% Gauge Length (g) | Load at 50% STS Elongation (g) |
|---|---|---|---|
| COHESIVE SBL | 130 | 730.3 | 874.2 |
| VETRAP ® | 100 | 326.2 | 326.2 |
| EQUISPORT ™ | 140 | 983.6 | 1276.0 |

TABLE 10

SELF-ADHESIVE MATERIALS
AGED 1 WEEK AT 147.6° F.

| Material | STS (%) | Load at 50% Gauge Length (g) | Load at 50% STS Elongation (g) |
|---|---|---|---|
| COHESIVE SBL | 130 | 785.1 | 937.9 |
| VETRAP ® | 100 | 451.2 | 451.2 |
| EQUISPORT ™ | 140 | 948.7 | 1220.0 |

TABLE 11

SELF-ADHESIVE MATERIALS
AGED 6 HOURS AT 204.8° F.

| Material | STS (%) | Load at 50% Gauge Length (g) | Load at 50% STS Elongation (g) |
|---|---|---|---|
| COHESIVE SBL | 130 | 1195.0 | 1405.0 |
| VETRAP ® | 100 | 361.6 | 361.6 |
| EQUISPORT ™ | 140 | 963.4 | 1233.0 |

TABLE 12

SELF-ADHESIVE MATERIALS
AGED 24 HOURS AT 204.8° F.

| Material | STS (%) | Load at 50% Gauge Length (g) | Load at 50% STS Elongation (g) |
|---|---|---|---|
| COHESIVE SBL | 130 | 1296.0 | 1507.0 |
| VETRAP ® | 100 | 342.8 | 342.8 |
| EQUISPORT ™ | 140 | 930.7 | 1189.0 |

TABLE 13

SELF-ADHESIVE MATERIALS
AGED 1 WEEK AT 204.8° F.

| Material | STS (%) | Load at 50% Gauge Length (g) | Load at 50% STS Elongation (g) |
|---|---|---|---|
| COHESIVE SBL | 130 | 1121.0 | 1379.0 |
| VETRAP ® | 100 | 185.8 | 185.8 |
| EQUISPORT ™ | 140 | 720.6 | 936.4 |

COMPRESSION TESTING OF SELF-ADHESIVE ELASTIC MATERIALS

The compressibility of various self-adhesive composite elastic materials were measured utilizing a Standard Model Compressometer available from the Frazier Precision Instrument Company of Gaithersburg, Md. The Compressometer was fitted with a 3 inch diameter circular foot and air pressure was applied to a piston which connected to the foot. Air pressure was regulated to provide a specific compression force exerted by the foot onto the sample. Each sample was larger than the 3 inch diameter circular foot. An interval of about 5 to 10 seconds was taken between readings to allow the pressure in the piston to reach the desired level. Two thickness are reported. The first thickness was the thickness measured at the correct pressure as the pressure was increased from about 0 psi. The second thickness was the thickness measured at the correct pressure as the pressure was decreased from about 3.0 psi. The values reported in Table 14 represent an average of results reported for 5 samples. The results are reported in inches.

The sample materials were VETRAP® and EQUI-SPORT™ self-adhesive wrapping materials, available from the Minnesota Mining and Manufacturing Company; CO-FLEX® cohesive flexible bandage wrapping material available from Andover Coating Company of Salisbury, Massachusetts. The other material was the self-adhesive elastic composite material formed from a stretch bonded laminate material as described above for the tensile testing.

COMPRESSION TESTING RESULTS FOR SELF-ADHESIVE WRAPPING MATERIALS

| Material | PSI | | | | | | | | | |
|---|---|---|---|---|---|---|---|---|---|---|
| | 0.10 | 0.20 | 0.35 | 0.5 | 0.75 | 1.00 | 1.50 | 2.00 | 2.50 | 3.00 |
| CO-FLEX ® | | | | | | | | | | |
| Avg. Thickness* | 0.0640 | 0.0590 | 0.0570 | 0.0540 | 0.0510 | 0.0480 | 0.0440 | 0.0410 | 0.0360 | 0.0340 |
| Std. Deviation | 0.0022 | 0.0011 | 0.0016 | 0.0005 | 0.0000 | 0.0009 | 0.0008 | 0.0004 | 0.0036 | 0.0029 |
| Avg. Thickness | 0.0470 | 0.0430 | 0.0410 | 0.0400 | 0.0390 | 0.0360 | 0.0340 | 0.0330 | 0.0320 | 0.0320 |
| Std. Deviation | 0.0024 | 0.0035 | 0.0023 | 0.0023 | 0.0022 | 0.0023 | 0.0027 | 0.0021 | 0.0021 | 0.0024 |
| VETRAP ® | | | | | | | | | | |
| Avg. Thickness | 0.0580 | 0.0530 | 0.0510 | 0.0500 | 0.0480 | 0.0450 | 0.0420 | 0.0380 | 0.0360 | 0.0340 |
| Std. Deviation | 0.0042 | 0.0007 | 0.0008 | 0.0005 | 0.0026 | 0.0004 | 0.0005 | 0.0005 | 0.0008 | 0.0011 |
| Avg. Thickness | 0.0480 | 0.0450 | 0.0430 | 0.0410 | 0.0400 | 0.0390 | 0.0370 | 0.0340 | 0.0330 | 0.0330 |
| Std. Deviation | 0.0022 | 0.0020 | 0.0013 | 0.0011 | 0.0015 | 0.0022 | 0.0015 | 0.0013 | 0.0008 | 0.0008 |
| COHESIVE SBL | | | | | | | | | | |
| Avg. Thickness | 0.0070 | 0.0670 | 0.0660 | 0.0650 | 0.0610 | 0.0570 | 0.0520 | 0.0480 | 0.0430 | 0.0400 |
| Std. Deviation | 0.0023 | 0.0038 | 0.0044 | 0.0060 | 0.0028 | 0.0026 | 0.0029 | 0.0027 | 0.0036 | 0.0032 |
| Avg. Thickness | 0.0530 | 0.0500 | 0.0480 | 0.0460 | 0.0440 | 0.0430 | 0.0410 | 0.0390 | 0.0390 | 0.0380 |
| Std. Deviation | 0.0031 | 0.0037 | 0.0043 | 0.0037 | 0.0039 | 0.0042 | 0.0033 | 0.003 | 0.0025 | 0.0029 |
| EQUISPORT ™ | | | | | | | | | | |
| Avg. Thickness | 0.034 | 0.032 | 0.031 | 0.029 | 0.028 | 0.027 | 0.025 | 0.0230 | 0.022 | 0.021 |
| Std. Deviation | 0.0008 | 0.0008 | 0.0008 | 0.0009 | 0.001 | 0.0005 | 0.0 | 0.0008 | 0.0004 | 0.0004 |
| Avg. Thickness | 0.029 | 0.027 | 0.026 | 0.026 | 0.025 | 0.025 | 0.022 | 0.021 | 0.021 | 0.021 |
| Standard | 0.0005 | 0.0 | 0.0004 | 0.0004 | 0.0004 | 0.0005 | 0.0005 | 0.0005 | 0.0004 | 0.0005 |

\* = thickness is expressed in inches.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A self-adhesive nonwoven elastic composite material comprising:
   at least one elastic composite material comprising:
     at least one elastomeric nonwoven fibrous web, and
     at least one relatively nonelastic gatherable material joined to the elastomeric nonwoven fibrous web at spaced-apart locations so that the gatherable material is gathered between the spaced-apart locations; and
   a coating of a self-adhesive material on at least a portion of at least one exterior surface of the elastic composite material wherein the peel strength determined essentially in accordance with ASTM D 1876-72 of the self-adhesive material is at least about 5 percent less than the peel strength which binds the layers of the elastic composite material, and
   wherein the material is capable of being compressed in the Z-direction at least about 45 percent at a pressure of about 3 psi to a thickness of not less than about 0.035 inch.

2. The composite material of claim 1 wherein the peel strength determined essentially in accordance with ASTM D 1876-72 of the self-adhesive material is from about 10 about 98 percent less than the peel strength which binds the layers of the elastic composite material.

3. The composite material of claim 1 wherein the self-adhesive material is on a gatherable layer.

4. The composite material of claim 1 wherein the self-adhesive material is on a an elastomeric fibrous web.

5. The composite material of claim 3 wherein the self-adhesive material is located only on raised portions of the gathers present in the gatherable material.

6. The composite material of claim 1 wherein the self adhesive is in the form of a randomly scattered network of hot-melt adhesive filaments and fibers.

7. The composite material of claim 1 wherein the self adhesive is laid down in a semi-cycloidal pattern.

8. The composite material of claim of claim 1 having a basis weight ranging from about 40 to about 400 grams per square meter.

9. The composite material of claim of claim 8 having a basis weight ranging from about 100 to about 250 grams per square meter.

10. A self-adhesive product in the form of a wrap or bandage for use in human or veterinary medicine comprising the composite elastic material of claim 1.

11. A self-adhesive product in the form of a wrap or bandage for use in human or veterinary medicine comprising the composite elastic material of claim 8.

12. The self-adhesive product of claim 11 wherein the composite elastic material has a stretch-to-stop elongation of at least about 25 percent.

13. The self-adhesive product of claim 11 wherein the composite elastic material has a stretch-to-stop elongation ranging from about 35 percent to about 400 percent.

14. The composite material of claim 1 wherein the elastic composite material is capable of being compressed in the Z-direction at least about 35 percent at a pressure of about 1 psi to a thickness of not less than about 0.035 inch.

15. The composite material of claim 1 wherein the elastic composite material is capable of being compressed in the Z-direction at least about 55 percent at a pressure of about 3 psi to a thickness of not less than about 0.035 inch.

16. The composite material of claim 1 wherein the elastic composite material is capable of being compressed in the Z-direction at least about 55 percent at a pressure of about 3 psi to a thickness of ranging from about 0.040 inch to about 0.2 inch.

* * * * *